United States Patent
Sen et al.

(10) Patent No.: US 6,489,416 B2
(45) Date of Patent: Dec. 3, 2002

(54) PROCESS FOR SYNTHESIZING LINEAR POLYMERS OF ETHYLENE AND ALPHA-OLEFINS

(75) Inventors: Ayusman Sen, State College, PA (US); Louis M. Wojcinski, II, Chapel Hill, NC (US); Shengsheng Liu, State College, PA (US)

(73) Assignee: The Penn State Research Foundation, University Park, PA (US)

(*) Notice: Subject to any disclaimer, the term of this patent is extended or adjusted under 35 U.S.C. 154(b) by 72 days.

(21) Appl. No.: 09/778,966

(22) Filed: Feb. 7, 2001

(65) Prior Publication Data

US 2001/0031844 A1 Oct. 18, 2001

Related U.S. Application Data

(63) Continuation-in-part of application No. 09/273,128, filed on Mar. 19, 1999, now Pat. No. 6,291,387.
(60) Provisional application No. 60/078,695, filed on Mar. 20, 1998.

(51) Int. Cl.$^7$ ................................................. C08F 4/52
(52) U.S. Cl. ........................ 526/196; 526/185; 526/186; 526/189; 526/198; 502/152
(58) Field of Search ................................ 526/185, 186, 526/189, 196, 198

(56) References Cited

U.S. PATENT DOCUMENTS

| | | | |
|---|---|---|---|
| 2,744,074 A | 5/1956 | Theobald | 260/2 |
| 2,825,721 A | 3/1958 | Hogan et al. | 260/88.1 |
| 3,135,706 A | 6/1964 | Vandenberg | 260/2 |
| 5,340,892 A | 8/1994 | Kuramoto | 526/119 |
| 5,391,793 A | 2/1995 | Marks et al. | 556/179 |
| 5,777,120 A | * 7/1998 | Jordan et al. | 546/2 |
| 5,939,346 A | 8/1999 | Marks et al. | 502/103 |
| 5,962,362 A | 10/1999 | Wasserman et al. | 502/117 |

FOREIGN PATENT DOCUMENTS

| | | |
|---|---|---|
| JP | 2035-192 | 3/1977 |
| WO | WO 98/40421 | 9/1798 |
| WO | WO 94/10180 | 5/1994 |
| WO | WO 96/23010 | 8/1996 |

OTHER PUBLICATIONS

Chromocene Catalysts for Ethylene Polymerization: Scope of the Polymerization, *J. Poly. Sci.*, Part A; vol. 10, pp 2621–2637, Karol et al., 1972.
Preparation of "Living" Polypropylenes by a Soluble Vanadium–based Ziegler Catalyst, *Makromol. Chem.*, vol. 180, pp 1359–1361, Doi et al., 1979.
Ziegler–Natta Catalysis, *Advances in Organometallic Chemistry*, vol. 18, pp 99–149, Sinn et al., 1980.
New Pd(II)–and Ni(II)–Based Catalysts for Polymerization of Ethylene and α–Olefins, *J. Am. Chem. Soc.*, vol. 117, pp 6414–6415, Johnson et al., 1995.
Highly Active Iron and Cobalt Catalysts for the Polymerization of Ethylene, *J. Am. Chem. Soc.*, vol. 120, pp 4040–4050, Small et al., 1998.
High–Molecular–Weight Polyethylene: Growth Reactions at bis(dichloroaluminum)ethane and Trialkylaluminum, *Makromol. Chem.*, vol. 193, pp 1283–1288, Martin et al., 1992.
Cationic Aluminum Alkyl Complexes Incorporating Amidinate Ligands. Transition–metal–Free Ethylene Polymerization Catalysts, *J. Am. Chem. Soc.*, vol. 119, pp 8125–8126, Coles et al., 1997.
Synthesis and Structures of Mono— and Bis(amidinate) Complexes of Aluminum, *Organometallics*, vol. 16, pp 5183–5194, Coles et al., 1997.
Aluminum Alkyl Complexes Containing Guanidinate Ligands, *Organometallics*, vol. 17, pp 3265–3270, Aeilts et al., 1998.
Aluminum Complexes Incorporating Bulky Nitrogen and Sulfur Donor Ligands, *Organometallics*, vol. 17, pp 4042–4048, Coles et al., 1998.
Cationic Aluminum Alkyl Complexes Incorporating Aminotroponiminate Ligands, *J. Am. Chem. Soc.*, vol. 120, pp 8277–8278, Ihara et al., 1998.
Cationic Alkyl Aluminum Ethylene Polymerization Catalysts Based on Monoanionic N,N,N–pyridyliminoamide Ligands, *J. Chem. Commun.*, pp 2523–2524, Bruce et al., 1998.
Pendandt Arm Schiff Base Complexes of Aluminum as Ethylene Polymerization Catalysts, *J. Chem. Commun.*, pp 1883–1884, Cameron et al., 1999.
Novel Aluminum–Based Transition Metal–Free Catalytic Systems for Homo–and Copolymerization of Alkenes, *J. Am. Chem. Soc.*, vol. 122, pp 5668–5669, Kim et al., 2000.
Ziegler–Natta Catalyst Activation. Thermodynamic and Kinetic Aspects of Metallocenium Ion–Pair Formation, Dissociation, and Structural Reorganization, *Topics in Catalysis*, vol. 7, pp 97–106, Luo et al., 1999.
Polyethylene Polymerization, *Chem. Abs.*, vol. 49, p 3576e, Zeigler, 1954.

* cited by examiner

*Primary Examiner*—David W. Wu
*Assistant Examiner*—R. Rabago
(74) *Attorney, Agent, or Firm*—Anthony J. DeLaurentis

(57) ABSTRACT

Ethylene and/or propylene are polymerized to form high molecular weight, linear polymers by contacting ethylene and/or propylene monomer, in the presence of an inert reaction medium, with a catalyst system which consists essentially of (1) an aluminum alkyl component, such as trimethylaluminum, triethylaluminum, triisobutylaluminum, tri-n-octylaluminum and diethylaluminum hydride and (2) a Lewis acid or Lewis acid derivative component, such as $B(C_6F_5)_3$, $\{(CH_3)_2N(H)(C_6H_5)\}^+\{B(C_6F_5)_4\}^-$, $\{(C_2H_5)_3NH\}^+\{B(C_6F_5)_4\}^-$, $\{(C_6F_5)_3C\}^+\{B(C_6F_5)_4\}^-$, $\{(C_6F_5)_3C\}^+\{B(C_6F_5)_3(Cl)^-\}$, $(C_2H_5)_2Al(OCH_3)$, $(C_2H_5)_2Al(2,6-di-t-butyl-4-methylphenoxide)$, $(C_2H_5)Al(2,6-di-t-butylphenoxide)_2$, $(C_2H_5)_2Al(2,6-di-t-butylphenoxide)$, 2,6-di-t butylphenol.methyl-aluminoxane or an alkylaluminoxane, and which may be completely free any transition metal component(s).

19 Claims, No Drawings

PROCESS FOR SYNTHESIZING LINEAR POLYMERS OF ETHYLENE AND ALPHA-OLEFINS

RELATED APPLICATIONS

This application is a continuation-in-part of Ser. No. 09/273,128, filed Mar. 19, 1999, now U.S. Pat. No. 6,291,387, and is based on Provisional Application No.60/078,695, filed Mar. 20, 1998, the disclosures of which are incorporated herein by reference.

This application was funded under Department of Energy Contract No. DE-FG02-84ER13295.

BACKGROUND OF THE INVENTION

This invention relates to high molecular weight, highly linear polymers of ethylene and α-olefins, e.g., propylene, which are prepared in the presence of an aluminum-based catalyst system. More specifically, the invention relates to the synthesis of ethylene and α-olefin homopolymers and copolymers in an inert reaction medium in the presence of a catalyst system consisting essentially of an aluminum alkyl compound and a Lewis acid component. An advantage of the present invention is that it enables the synthesis of high molecular weight ethylene and α-olefin polymers without the need for transition metal catalysts, thereby avoiding disposal problems associated with the use of such catalysts.

It is known that the "aufbau" reaction, in which ethylene is reacted at high temperatures and high pressures to form higher olefins, occurs in two steps. In the first step, ethylene is exposed to a trialkyl aluminum compound at temperatures on the order of 90–120° C. and pressures of about 100 psi to form higher aluminum alkyls. In the second step, the temperature is raised to 150° C. to displace the higher alkyl groups and to form an α-olefin. While studying this reaction in the early 1950's, it was discovered that the addition to the reaction mass of earlier transition metal compounds, specifically titanium halides, resulted in the formation of high molecular polymers. Since that discovery, a variety of catalyst systems have been reported. using a variety of transisiton metals, including chromium (IV) oxides (Hogan, J. P., et al, *U.S. Pat. No.* 2,825,721), chromocenes (Karol, F. J., et al, *J. Polym. Sci., Part A*, 1972, 2621), and acetylacetonate complexes of vanadium (Doi, Y., et al, *Makromol. Chem.*, 1979, 180, 1359). Beginning in about 1980, a great deal of study was conducted in connection with highly active metallocene/methylaluminoxane (MAO) olefin polymerization catalyst systems, and more recently olefin polymerization catalysts based on diimine complexes of nickel and palladium have been reported. See, e.g., Sinn, H. and Kaminski, W., *Adv. Organomet. Chem.*, 1980, 18, 99; Johnson, L. K., et al, *J. Am. Chem. Soc.*, 1995, 117, 6414; Johnson, L. K., et al,*Int. Pat. Appl.* W096/23010 (1996); and Small, B. L., et al, *J. Am. Chem. Soc.*, 1998, 120,4049.

For each of the known transition metal-based catalyst systems, it was believed that the transition metal played a vital role in the formation of high molecular weight polymers; and that in the absence of any transition metal, only oligomers would be produced, as in the aufbau reaction. To date, there have been few reports detailing the preparation of high molecular polymers of ethylene via transition metal-free catalyst systems. In 1992, Heinz Martin (a former student of Karl Ziegler) reported the sysnthesis of high molecular weight polyethylene by exposing ethylene to an aluminum alkyl catalyst over a period of several days (Martin, H., *Makromol. Chem.*, 1992, 193, 1283). More recently, the synthesis of cationic aluminum complexes bearing bulky imine type ligands, as well as their potential utility as ethylene polymerization catalysts, has been investigated. See, e.g., Coles, M. P., et al, *J. Am. Chem. Soc.*, 1997, 119, 8125; Coles, M. P., et al. *Int. Pat. Appl.* W098/40421; Coles, M. P., et al, *Organometallics*, 1997, 16, 5183; Aielts, S. L., et al, *Organometallics*, 1998, 17, 3265; Coles, M. P., et al, *Organometallics*, 1998. 17. 4042; Ihara, E., et al, *J. Am. Chem. Soc.*, 1998, 120, 8277; Bruce, M., et al, *J. Chem. Commun.*, 1998, 2523; Cameron, P. A., et al, *Chem. Commun.*, 1999, 1883; Kim, J. S., et al, *J. Am. Chem. Soc.*, 2000, 122, 5668; and U.S. Pat. No. 5,777,120.

While great strides have been made in the search for new and improved ethylene and α-olefin polymerization catalysts, there remains a need for catalyst systems that are free from transition metals, that comprise only commercially available components, that require no ligand substitution, and that, nonetheless, are capable of efficiently converting monomer to high molecular weight polymer under otherwise conventional polymerization reaction conditions.

SUMMARY OF THE INVENTION

In accordance with the present invention, the need for transition metal-free olefin polymerization catalysts has been met by providing a catalyst system that comprises two essential components, namely: (1) an aluminum alkyl component, and (2) a Lewis acid or Lewis acid derivative component that is capable of activating the aluminum alkyl component.

The aluminum alkyl component may be illustrated by the formula $AlR_xH_{3-x}$, where R is an alkyl group, and $0<x\leq3$. Aluminum alkyl compounds that are suitable for use in this invention include, for example, trimethylaluminum, triethylaluminum, triisobutylaluminum, tri-n-octylaluminum and diethylaluminum hydride.

The Lewis acid component contemplated for use in this invention includes Lewis acids and Lewis acid derivatives having a relative Lewis acidity equal to or stronger than that of Tris-(pentafluorophenyl) boron (designated herein as "FAB" and having the formula $B(C_6F_5)_3$)), as determined from 1H NMR spectra of the Lewis acid or Lewis acid derivative based on $H_3$ chemical shift changes in crotonaldehyde when the latter is bound to the respective Lewis acid or Lewis acid derivative. The determination of the relative strength of a given Lewis acid or Lewis acid derivative is discussed more fully, for example, in Luo et al, *Topics in Catalvsis*, 1999, 7, 97, the disclosure of which is incorporated herein by reference. Lewis acid derivatives contemplated for use in this invention are those derivatives that are formed when a hydrocarbyl or halide ion is added to a Lewis acid. For example, when $C_6F_5^-$ or $Cl^-$ is added to $B(C_6F_5)_3$, the anionic derivatives $B(C_6F_5)_4^-$ and $B(C_6F_5)_3(Cl)^-$, respectively, would be the Lewis acid derivatives.

Thus, the Lewis acid or Lewis acid derivative component, hereinafter sometimes referred to as the "Lewis acid component", contemplated for use in the present invention includes for example, tris-(pentafluorophenyl) boron (designated herein as "FAB" and having the formula $B(C_6F_5)_3$)), tri(phenyl)methyl tetra(pentafluorophenyl) borate (designated herein as "Trityl FAB" and having the formula $\{(C_6F_5)_3C\}^+\{B(C_6F_5)_4\}^-$), N,N-dimethylanilinium tetra(pentafluorophenyl)borate (designated herein as "Anilinium FAB" and having the formula $\{(CH_3)_2N(H)(C_6H_5)\}^+\{B(C_6F_5)_4\}^-$), tri(phenyl)methyl tri(pentafluorophenyl)(chloro)borate (having the formula $\{(C_6F_5)_3C\}^+\{B(C_6F_5)_3(Cl)^-\}$) or a conventional alkylaluminoxane, such as methylaluminoxane (designated herein as "MAO" and having the formula $-(Al(CH_3)O)_n-$.

MAO, which is the product of the hydrolysis of trimethylaluminum, contains as much as 30% unreacted aluminum trialkyl. Accordingly, it is within the scope of this invention to use MAO as both the aluminum alkyl component and as the Lewis acid component of the catalyst system. However, in such case, it is preferable to add an aluminum alkyl component and/or a Lewis acid component in addition to the MAO. Similarly, it is also within the scope of this invention to use an alkylaluminoxane in conjunction with an alcohol or phenol adduct of an alkylaluminoxane. For example, a suitable catalyst system in accordance with this invention would comprise MAO in combination with 2,6-di-t-butylphenol.MAO.

The catalyst system of this invention is indeed capable of polymerizing ethylene and α-olefins, particularly propylene, under conventional reaction conditions, and results in the formation of high molecular weight, highly linear polymers having narrow polydispersities, indicative of a "single site" catalyst.

The polymerization typically is carried out by contacting the selected monomer (e.g., ethylene and/or propylene) in an inert polar solvent (e.g., chlorobenzene) or hydrocarbon solvent (e.g., toluene) at a temperature of about 20 to 150° C., typically from about 50 to about 120° C., e.g. 50° C, and a pressure of from about 50 to about 1,500 psi, typically from about 400 to about 800 psi, e.g., 800 psi. The polymerization reaction typically would be allowed to proceed for a period of from about 1 hour to about 24 hours, after which the polymerization reaction would be terminated by conventional means, e.g., by adding methanol or another conventional polymerization stopper to the reaction mass.

DESCRIPTION OF PREFERRED EMBODIMENTS

The preparation of high molecular weight, essentially linear polymers (as determined by H and C-NMR and by a melting point greater than 133° C.) of ethylene and α-olefins, e.g., propylene, is achieved in accordance with one preferred aspect of the invention by contacting ethylene and/or propylene, in the presence of an inert solvent, and under polymerization reaction conditions, with a catalyst which comprises (1) an alkylaluminum component and (2) a Lewis acid or Lewis acid derivative component as the only essential components.

The monomers that may be polymerized in accordance with this invention include ethylene and propylene, as well as other (x-olefins, such as hexene.

The monomers may be polymerized singly to form homopolymers, such as polyethylene or polypropylene. In the alternative, two or more monomers may be mixed and polymerized simultaneously to form copolymers, such as ethylene-propylene copolymers. Typically, the present invention would be used to prepare polyethylene and polypropylene products having a number average molecular weight ($M_n$), determined relative to polystyrene standards, on the order of from about 5,000 to about 500,000, preferably from about 20,000 to about 200,000. The resulting polymer products would be highly linear and would be characterized by a narrow polydispersity ($M_w/M_n$), typically on the order of from about 1.5 to about 2.5, indicative of a single site catalyst.

The polymerization preferably is carried out in the presence of an inert solvent, with polar solvents, such as chlorobenzene, being preferred over hydrocarbon solvents, such as toluene, inasmuch as the use of polar solvents has been found to result in a higher yield of polymer product.

Polar solvents, which may be used in lieu of chlorobenzene, or in addition to chlorobenzene include, for example, dichlorobenzene, trichlorobenzene and tetrachloroethane.

Hydrocarbon solvents, which may be used in lieu of toluene, or in addition to toluene include, for example, benzene, xylene and hexane.

The polymerization typically is carried out by contacting the selected monomer and the catalyst system at a temperature of about 20 to 150° C., typically from about 50 to about 120° C., e.g. 50° C., and at a pressure of from about 50 to about 1,500 psi, typically from about 400 to about 800 psi, e.g., 800 psi. The polymerization may be performed in conventional apparatus and in a conventional manner, except that the present catalyst system would be used in place of the currently employed transition metal-based catalyst systems. The polymerization may be performed in a continuous process, a semi-continuous process, or a batch process, as desired. Typically, the polymerization would be allowed to proceed for a period of from about 1 hour to about 24 hours, after which the polymerization reaction would be terminated by conventional means, e.g., by adding methanol or another conventional polymerization stopper to the reaction mass.

The catalyst system of this invention does not require the presence of a transition metal component. The only essential components of the catalyst system are (1) an aluminum alkyl component and (2) a Lewis acid or Lewis acid derivative component that is capable of activating the aluminum alkyl component.

The aluminum alkyl component may be any conventional aluminum alkyl and may be illustrated by the formula $AlR_xH_{3-x}$ where R is an alkyl group, typically a $C_1$–$C_{10}$ alkyl group, and $0 < x \leq 3$. Aluminum alkyl compounds that are suitable for use in this invention include, for example, trimethylaluminum, triethylaluminum, triisobutylaluminum, and tri-n-octylaluminum and diethylaluminum hydride.

As used in this specification and claims, the term Lewis acid or Lewis acid derivative, sometimes referred to as the "Lewis acid component", is meant to describe any relative strong Lewis acid or Lewis acid derivative that is capable of activating the aluminum alkyl component to the extent that the desired polymerization will occur with reasonable efficiency. Typically, the Lewis acid or Lewis acid derivative will be selected such that the polymerization activity of the resulting catalyst system is on the order of from about 0.01 to about 100 kg/mol catalyst.hr.

In keeping with this requirement, Lewis acids and Lewis acid derivatives which have been found to be useful in this invention are those Lewis acids and Lewis acid derivatives having a relative Lewis acidity equal to or stronger than that of tris-(pentafluorophenyl) boron (designated herein as "FAB" and having the formula $B(C_6F_5)_3$)), as determined from 1H NMR spectra of the Lewis acid or Lewis acid derivative based on $H_3$ chemical shift changes in crotonaldehyde when the latter is bound to the respective Lewis acid or Lewis acid derivative. The determination of the relative strength of a given Lewis acid or Lewis acid derivative is discussed more fully, for example, in Luo et al, *Topics in Catalysis*, 1999, 7, 97, the disclosure of which is incorporated herein by reference. Lewis acid derivatives contemplated for use in this invention are those derivatives that are formed when a hydrocarbyl or halide ion is added to a Lewis acid. For example, when $C_6F_5^-$ or $Cl^-$ is added to $B(C_6F_5)_3$, the anionic derivatives $B(C_6F_5)_4^-$ and $B(C_6F_5)_3(Cl)^-$, respectively, would be the Lewis acid derivatives.

The Lewis acids and Lewis acid derivatives which have been found to be particularly suitable for use in this invention include, for example, relatively strong organoboron or organoaluminum compounds, such as Tris-(pentafluorophenyl) boron (designated herein as "FAB" and having the formula $B(C_6F_5)_3$)), tri(phenyl)methyl tetra (pentafluorophenyl)borate (designated herein as "Trityl FAB" and having the formula $\{(C_6F_5)_3C\}^+\{B(C_6F_5)_4\}^-)$, N,N-dimethylanilinium tetra(pentafluorophenyl)borate (designated herein as "Anilinium FAB" and having the formula $\{(CH_3)_2N(H)(C_6H_5)\}^+\{B(C_6F_5)_4\}^-)$, triethylammonium tetra-(pentafluorophenyl)borate (having the formula $\{(C_2H_5)_3NH\}^+\{B(C_6F_5)_4\}^-)$, and tri(phenyl)methyl tri (pentafluorophenyl)(chloro)borate (having the formula $\{(C_6F_5)_3C\}^+\{B(C_6)_3(Cl)^-\})$. Additional, non-limiting examples of Lewis acids or Lewis acid derivatives that may be used as part of the present catalyst system include, for example, diethylaluminum methoxide $(C_2H_5)_2Al(OCH_3)$, diethylaluminum-2,6-di-t-butyl-4-methylphenoxide $(C_2H_5)_2Al(2,6-di-t-butyl-4-methylphenoxide)$, ethylaluminum-di-(2,6-di-t-butyl-4-methylphenoxide) $(C_2H_5)Al(2,6-di-t-butylphenoxide)_2$, diethylaluminum-(2,6-di-t-butylphenoxide) $(C_2H_5)_2Al(2,6-di-t-butylphenoxide)$, as well as conventional alkylaluminoxanes, such as methylaluminoxane (designated herein as "MAO" and having the formula $—(Al(CH_3)O)_n—)$.

It should be noted that the alkylaluminoxanes, which are the product of the hydrolysis of a trialkylaluminum, e.g., trimethylaluminum in the case of MAO, and which contain as much as 30% unreacted trialkylaluminum, function both as the aluminum alkyl component and as the organo-Lewis acid component of the catalyst system. Accordingly, it is within the scope of this invention to use an alkylaluminoxane as the sole catalyst component. However, when use is made of an alkylaluminoxane as a catalyst component of this invention, it is preferable to add an aluminum alkyl component in addition to the alkylaluminoxane. Similarly, it is also within the scope of this invention to use an alkylaluminoxane component in conjunction with an alcohol or phenol adduct of an alkylaluminoxane. For example, a suitable catalyst system in accordance with this latter aspect of the invention would comprise MAO in combination with the 2,6-di-t-butylphenol.MAO adduct.

The invention will be appreciated more fully in light of the following examples, which are intended merely to illustrate the invention, and not to limit the scope thereof.

EXAMPLE 1

Ethylene polymerization via Transition Metal-Free Catalyst

In a series of polymerization runs, ethylene was polymerized at 50–60° C. in the presence of the catalyst system and reaction solvent indicated in Table 1. Each polymerization run was carried out in a stainless steel 125 ml pressure vessel equipped with a glass liner. For most runs, the catalyst system, mixed in 10 ml of solvent, was introduced into the pressure vessel in a nitrogen-filled glove box. Then, after removing the assembled pressure vessel from the glove box, the vessel was charged with 800 psi ethylene (single charge), and the reaction was allowed to continue for the indicated time. The reaction vessel was then vented, and the reaction mixture was poured, with stirring, into acidic methanol to kill the polymerization. The polymer was stirred overnight, filtered, and vacuum dried overnight. For each run, the resulting polymer was analyzed by $^1H$ NMR, by $^{13}C$ NMR, by gel permeation chromatography (GPC) and by differential scanning calorimetry (DSC) techniques. The polymer was analyzed for yield, activity, number average molecular weight ($M_n$) and weight average molecular weight ($M_w$). The molecular weights were determined by gel permeation chromatography (GPC) using a Waters 150C apparatus with an index refractometer (IR) detector and polystyrene standards. The measurements were carried out either at 140° C. using 1,2,4-t richlorobenzene (TCB) as solvent or at 25° C. using chloroform as solvent. All high temperature $^1H$ NMR and $^{13}C$ NMR data was recorded on a Bunker AM-300 spectrometer with DISNMR software. The measurements were obtained at 110° C. using $C_2D_2Cl_4$ or $C_6D_5Cl$ as the solvent containing 1% TMS ($Me_4Si$ ($\delta$=0.00 ppm)) as an external standard. Differential scanning calorimetry (DSC) was measured on a Perkin Elmer DSC-7 instrument. The data observed for each run is set forth in Table 1.

TABLE 1

Ethylene polymerization via transition metal-free catalysis

| Run No. | Catalyst | Components | Solvent | Yield (g) | Activity (kg/mol cat-alyst · hr) | $M_n°$ (× $10^{-3}$) | $M_w°$ (× $10^{-3}$) |
|---|---|---|---|---|---|---|---|
| 1 | $Al(C_2H_5)_3{}^a$ | $MAO^h$ | $C_6H_5Cl$ | 3.9 | 3.25 | 40 $111^b$ | 98 263 |
| 2 | $Al(C_2H_5)_3{}^a$ | $MAO^h$ | Toluene | 0.6 | 0.50 | | |
| 3 | $MAO^{a,h}$ | $FAB^i$ | $C_6H_5Cl$ | 0.4 | 0.35 | 282 | 486 |
| 4 | $Al(C_2H_5)_3{}^a$ | $FAB^i$ | $C_6H_5Cl$ | 1.0 | 0.85 | | |
| 5 | $Al(C_2H_5)_3{}^a$ | Trityl $FAB^j$ | $C_6H_5Cl$ | 2.8 | 2.46 | | |
| 6 | $Al(C_2H_5)_3{}^a$ | an. $FAB^k$ | $C_6H_5Cl$ | 1.1 | 1.03 | | |
| 7 | $Al(CH_3)_3{}^a$ | $MAO^h$ | $C_6H_5Cl$ | 1.5 | 1.25 | | |
| 8 | $(i-C_4H_9)_2AlH^a$ | $FAB^i$ | $C_6H_5Cl$ | 0.6 | 0.50 | | |
| 9 | $MAO^{c,h}$ | $FAB^i$ | Toluene | 1.2 | 1.00 | | |
| 10 | $MAO^{c,h}$ | an. $FAB^k$ | $C_6H_5Cl$ | 0.9 | 0.75 | | |
| 11 | $MAO^{d,h}$ | $(C_2H_5)_2Al(OC_2H_5)$ | $C_6H_5Cl$ | 0.3 | 0.01 | | |
| 12 | $MAO^{e,h}$ | $(C_2H_5)Al(dt-bmp)^l$ | $C_6H_5Cl$ | 0.2 | 0.02 | | |
| 13 | $MAO^{f,h}$ | $(C_2H_5)Al(dtbp)^m$ | $C_6H_5Cl$ | 2.4 | 0.13 | | |
| 14 | $MAO^{g,h}$ | $(C_2H_5)Al(dtbp)^m$ | $C_6H_5Cl$ | 4.7 | 1.04 | | |
| 15 | $MAO^{f,h}$ | dtbp · $MAO^n$ | $C_6H_5Cl$ | 2.5 | 0.14 | | |

Reaction conditions run with 800 psi ethylene (single charge). $^a$=0.3 mmol each catalyst component, 50° C., 4 hrs., 10 ml solvent. $^b$=Reaction run for 20 hrs. $^c$=0.4 mmol each alyst component, 50° C., 4 hrs., 20 ml solvent. $^d$=3 mmols each catalyst component, 60° C., 10 hrs., 10 ml solvent. $^e$=2 mmol each catalyst component, 5 hrs. $^f$=2 mmol each catalyst component, 9 hrs. $^g$=0.5 mmol each catalyst component, 9 hrs. $^h$=MAO methylaluminoxane. i=FAB=B $(C_6F_5)_3$=Tris(pentafluorophenyl)boron. $^j$=Trityl FAB= $[(C_6F_5)_3C]^+[B[(C_6F_5)_4]^-$=Tri(phenyl)methyltetra (pentafluorophenyl)borate. $^k$=an. FAB=Anilinium FAB= $[(CH_3)_2N(H)(C_6H_5)]^+[B[(C_6F_5)_4]^-$=N,N-dimethylanilinium tetra(pentafluorophenyl)borate. $^l$=dtbmp=2,6-di-t-butyl-4-hylphenoxide. $^m$=dtbp=2,6-di-t-butylphenoxide. $^n$=adduct of MAO with 1 eq. 2,6-di-t-butylphenol. $^o$=Determined relative to polystyrene standards.

EXAMPLE 2

Propylene Polymerization

In a series of polymerization runs, propylene was polymerized in the presence of the catalyst system and reaction solvent indicated in Table 2. Each polymerization run was carried in a stainless steel 125 ml pressure vessel equipped with a glass liner. For each run, the catalyst system, mixed in 10 ml of solvent, was introduced into the pressure vessel in a nitrogen-filled glove box. Then, after removing the assembled pressure vessel from the glove box, the vessel was charged with 5 grams of propylene (single charge), and the reaction was allowed to continue at 50° C. for 20 hours in the presence of 0.3 mmol of each catalyst component indicated in Table 2. The reaction vessel was then vented, and the reaction mixture was poured, with stirring, into acidic methanol to kill the polymerization. The polymer was stirred overnight, filtered, and vacuum dried overnight. For each run, the resulting polymer was analyzed for yield, activity, number average molecular weight ($M_n$) and weight average molecular weight ($M_w$) using the procedures set forth in Example 1. The data observed for each run is set forth in Table 2.

TABLE 2

Propylene polymerization

| Run No. | Catalyst | Components | Solvent | Yield (g) | Activity (kg/mol catalyst · hr) | $M_n°$ (× 10$^{-3}$) | $M_w°$ (× 10$^{-3}$) |
|---|---|---|---|---|---|---|---|
| 1 | Al(C$_2$H$_5$)$_3$ | B(C$_6$F$_5$)$_3$ | C$_6$H$_5$Cl | 0.71 | 0.10 | 74 | 140 |
| 2 | MAO$^a$ | B(C$_6$F$_5$)$_3$ | Toluene | 0.95 | 0.13 | 112 | 229 |
| 3 | Al(CH$_3$)$_3$ | B(C$_6$F$_5$)$_3$ | C$_6$H$_5$Cl | 0.20 | 0.03 | | |
| 4 | (i-Butyl)$_2$AlH | an. FAB$^b$ | C$_6$H$_5$Cl | 0.07 | 0.01 | | |

Reactions were run with a single 5 gram charge of propylene.
$^a$= MAO = methylaluminoxane.
$^b$= an. FAB = Anilinium FAB = [(CH$_3$)$_2$N(H)(C$_6$H$_5$)]$^+$[B[(C$_6$F$_5$)$_4$]$^-$ = N,N-dimethylanilinium tetra(penafluorophenyl)borate.
$^c$= Determined relative to polystyrene standards.

EXAMPLE 3

Ethylene/Propylene Copolymerization Using an. FAB/ Al(C$_2$H$_5$)$_3$

In a series of polymerization runs, ethylene and propylene was copolymerized at 60° C. in the presence of the catalyst system and reaction solvent indicated in Table 3. Each polymerization run was carried in a stainless steel 125 ml pressure vessel equipped with a glass liner. For each run, the catalyst system, mixed in 10 ml of solvent, was introduced into the pressure vessel in a nitrogen-filled glove box. Then, after removing the assembled pressure vessel from the glove box, the vessel was charged with the indicated pressures of ethylene and propylene (single charge for each), and the reaction was allowed to continue for the indicated time. The reaction vessel was then vented, and the reaction mixture was poured, with stirring, into acidic methanol to kill the polymerization. The polymer was stirred overnight, filtered, and vacuum dried overnight. For each run, the resulting polymer was analyzed for yield, activity, and melting point. The data observed for each run is set forth in Table 3.

TABLE 3

Ethylene/propylene copolymerization

| Run | Ethylene (psi) | Propylene (psi) | Time (hrs.) | Yield (g) | $T_m$ (melting point) (° C.) | Propylene (mol %) |
|---|---|---|---|---|---|---|
| 1 | 700 | 0 | 1.5 | 1.84 | 135.9 | 0 |
| 2 | 400 | 100 | 5 | 4.39 | 121.6 | 4.67 |
| 3 | 300 | 100 | 5 | 2.50 | 115.6 | 5.40 |
| 4 | 150 | 100 | 5 | 0.70 | 108.5 | 5.88 |
| 5 | 50 | 100 | 5 | 0.05 | 53.4 | 16.9 |

Conditions for each run: 10 ml chlorobenzene solvent; 0.1 mmol anilinium FAB = [(CH$_3$)$_2$N(H)(C$_6$H$_5$)]$^+$[B[(C$_6$F$_5$)$_4$]$^-$ = N,N-dimethylanilinium tetra(pentafluorophenyl)borate, and 0.1 mmol Al(C$_2$H$_5$)$_3$; single charge ethylene/propylene.

What is claimed is:

1. A process for synthesizing linear polymers of ethylene and α-olefins, which comprises:
    contacting at least one monomer selected from the group consisting of ethylene and α-olefins, under polymerization reaction conditions and in the presence of an inert reaction medium, with a catalyst system consisting essentially of (1) an aluminum alkyl component and (2) a Lewis acid or a Lewis acid derivative component; and
    maintaining contact between said catalyst system and said at least one monomer for a period sufficient to produce a linear polymer therefrom.

2. The process according to claim 1, wherein said at least one monomer is selected from the group consisting of ethylene and propylene and mixtures thereof.

3. The process according to claim 1, wherein said aluminum alkyl is represented by the formula AlR$_x$H$_{3-x}$, where R is an alkyl group and $0<x\leq3$; and wherein said Lewis acid or Lewis acid derivative comprises at least one member selected from the group consisting of (a) B(C$_6$F$_5$)$_3$, (b) {(CH$_3$)$_2$N(H)(C$_6$H$_5$)}$^+${B(C$_6$F$_5$)$_4$}$^-$, (c) {(C$_2$H$_5$)$_3$NH}$^+${B(C$_6$F$_5$)$_4$}$^-$, (d) {(C$_6$F$_5$)$_3$C}$^+${B(C$_6$F$_5$)$_4$}$^-$, (e) {(C$_6$F$_5$)$_3$C}$^+${B(C$_6$F$_5$)$_3$(Cl)$^-$}, (f) (C$_2$H$_5$)$_2$Al(OCH$_3$), (g) (C$_2$H$_5$)$_2$Al(2,6-di-t-butyl-4-methylphenoxide), (h) (C$_2$H$_5$)Al(2,6-di-t-butylphenoxide)$_2$, (i) (C$_2$H$_5$)$_2$Al(2,6-di-t-butylphenoxide), (j)$_{2,6}$-di-t-butylphenol.methylaluminoxane and (k) an alkylaluminoxane.

4. The process according to claim 1, wherein said Lewis acid or Lewis acid derivative component comprises an alkylaluminoxane that contains unreacted aluminum trialkyl, such that said alkylaluminoxane functions as both said aluminum alkyl component and said Lewis acid component of said catalyst system.

5. The process according to claim 3, wherein said aluminoxane is selected from the group consisting of methylaluminoxane and an alcohol or phenol adduct of an aluminoxane.

6. The process according to claim 5, wherein said alcohol adduct comprises 2,6-di-t-butylphenol.methylaluminoxane.

7. The process according to claim 3, wherein said aluminum alkyl is selected from the group consisting of trimethyl aluminum, triethyl aluminum, triisobutyl aluminum, diisobutyl aluminum hydride and tri-n-octyl aluminum.

8. The process according to claim 2, wherein said inert reaction medium comprises a polar solvent.

9. The process according to claim 8, wherein said inert reaction medium comprises at least one member selected from the group consisting of chlorobenzene, dichlorobenzene, trichlorobenzene and tetrachloroethane.

10. The process according to claim 2, wherein said inert reaction medium comprises a hydrocarbon solvent.

11. The process according to claim 10, wherein said inert reaction medium comprises at least one member selected from the group consisting of toluene, benzene, xylene and hexane.

12. The process according to claim 3, wherein said inert reaction medium comprises a polar solvent.

13. The process according to claim 12, wherein said inert reaction medium comprises at least one member selected from the group consisting of chlorobenzene, dichlorobenzene, trichlorobenzene and tetrachloroethane.

14. The process according to claim 3, wherein said inert reaction medium comprises a hydrocarbon solvent.

15. The process according to claim 14, wherein said inert reaction medium comprises at least one member selected from the group consisting of toluene, benzene, xylene and hexane.

16. A process for synthesizing high molecular weight, linear polymer from ethylene, an α-olefin, or mixtures thereof, comprising:

contacting a monomer selected from the group consisting of ethylene, propylene and mixtures of ethylene and propylene, in the presence of an inert polar reaction medium and under polymerization reaction conditions, with a catalyst system consisting essentially of aluminum alkyl and a Lewis acid or Lewis acid derivative activator for said aluminum alkyl; and maintaining said contact for a period of time sufficient to form said linear polymer.

17. The process according to claim 16, wherein said aluminum alkyl is represented by the formula $AlR_xH_{3-x}$, where R is an alkyl group and $0<x\leq3$; and wherein said Lewis acid or Lewis acid derivative comprises at least one member selected from the group consisting of (a) $B(C_6F_5)_3$, (b) $\{(CH_3)_2N(H)(C_6H_5)\}^+\{B(C_6F_5)_4\}^-$, (c) $\{(C_2H_5)_3NH\}^+\{B(C_6F_5)_4\}^-$, (d) $\{(C_6F_5)_3C\}^+\{B(C_6F_5)4\}^-$, (e) $\{(C_6F_5)_3C\}^+\{B(C_6F_5)_3(Cl)^-\}$, (f) $(C_2H_5)_2Al(OCH_3)$, (g) $(C_2H_5)_2Al(2,6$-di-t-butyl-4-methylphenoxide), (h) $(C_2H_5)Al(2,6$-di-t-butylphenoxide)$_2$, (i) $(C_2H_5)_2Al(2,6$-di-t-butylphenoxide), (j)$_{2,6}$-di-t-butylphenol.methylaluminoxane and (k) an alkylaluminoxane.

18. The process according to claim 17, wherein said alkylaluminoxane is selected from the group consisting of methylaluminoxane and an alcohol or phenol adduct of an aluminoxane.

19. The process according to claim 18, wherein said alcohol or phenol adduct comprises 2,6-di-t-butylphenol-methylaluminoxane.

* * * * *